United States Patent
Sageser et al.

[11] Patent Number: 6,039,906
[45] Date of Patent: *Mar. 21, 2000

[54] METHOD FOR APERTURING A LAMINATE

[75] Inventors: David Mark Sageser, Cincinnati, Ohio; Takuya Shirakawa, Akashi; Koichi Morimoto, Hyogo, both of Japan

[73] Assignee: The Procter & Gamble Company, Cincinnati, Ohio

[ * ] Notice: This patent issued on a continued prosecution application filed under 37 CFR 1.53(d), and is subject to the twenty year patent term provisions of 35 U.S.C. 154(a)(2).

[21] Appl. No.: 08/920,958

[22] Filed: Aug. 29, 1997

[51] Int. Cl.⁷ .......................... B29C 55/00; B29C 61/02; B29C 59/04
[52] U.S. Cl. .......................... 264/156; 264/230; 264/237; 264/296; 264/322; 264/342 R; 264/348; 425/290
[58] Field of Search ..................... 264/154, 156, 264/284, 322, 342 R, 348, 230, 237, 296; 425/290, 294

[56] References Cited

U.S. PATENT DOCUMENTS

| | | |
|---|---|---|
| 3,187,380 | 6/1965 | Harrison .................................. 264/230 |
| 4,407,284 | 10/1983 | Pieniak .................................... 604/385 |
| 5,234,423 | 8/1993 | Alemany et al. .................... 604/385.2 |
| 5,296,184 | 3/1994 | Wu et al. ................................. 264/154 |
| 5,571,096 | 11/1996 | Dobrin et al. ......................... 604/383 |
| 5,628,097 | 5/1997 | Benson et al. ......................... 264/145 |
| 5,656,119 | 8/1997 | Srinivasan et al. ................... 156/290 |
| 5,704,101 | 1/1998 | Majors et al. .......................... 26/18.6 |

FOREIGN PATENT DOCUMENTS

EP 0 274 752
A2  7/1988   European Pat. Off.
WO 96/39109  12/1996   WIPO.

*Primary Examiner*—Jan H. Silbaugh
*Assistant Examiner*—Michael Poe
*Attorney, Agent, or Firm*—Kevin C. Johnson; Steven W. Miller; Jacobus C. Rasser

[57] ABSTRACT

A method for aperturing a laminate. The first step is to provide a laminate having at least one nonwoven web of thermoplastic fibers and at least one elastic member. The laminate is forwarded through a pressure biased nip having a relief patterned nip defining member having a plurality of pattern elements and a nip defining anvil member. The nip defining members are biased towards each other with a predetermined pattern-element loading. Each nip defining member is heated to a temperature that is sufficiently above the melt temperature of the thermoplastic fibers of the nonwoven web and above the melt temperature of the elastic member to enable aperturing of the laminate.

6 Claims, 4 Drawing Sheets

METHOD FOR APERTURING A LAMINATE

FIELD OF THE INVENTION

The present invention relates to a method for aperturing a laminate, at least one layer of which comprises thermoplastic material, and the other layer comprises an elastic member, and more particularly, to a method for aperturing portions of a disposable absorbent article comprising a nonwoven web comprised of thermoplastic fibers and an elastomeric film.

As used herein, the term "laminate" includes portions of disposable absorbent articles comprising two or more layers joined together, e.g., an elasticized waist feature which comprises an elastic member such as an elastomeric film affixed between the topsheet and the backsheet wherein the topsheet and/or the backsheet are comprised of a thermoplastic material.

BACKGROUND OF THE INVENTION

Infants and other incontinent individuals wear disposable absorbent articles such as diapers to receive and contain urine and other body exudates. Absorbent articles function both to contain the discharged materials and to isolate these materials from the body of the wearer and from the wearer's garments and bed clothing. Disposable absorbent articles having many different basic designs are known to the art.

However, absorbent articles have a tendency to sag or gap away from and to slide/slip down on the body of the wearer during wear. This sagging/gapping and sliding/slipping is caused by the relative motions of the wearer as the wearer breathes, moves and changes positions, by the downward forces generated when the absorbent article is loaded with body exudates, and by the deformation of the materials of the absorbent article itself when subjected to such wearer's motions. This sagging/gapping and sliding/slipping of the absorbent article can lead to premature leakage and poor fit of the absorbent article about the wearer in the waist regions and the leg regions of the absorbent article.

In order to more snugly fit absorbent articles about the wearer, certain commercially available absorbent articles have been provided with elastic waist features and elastic side panels. An example of a disposable diaper with elasticized waist features and elasticized side panels is disclosed in U.S. Pat. No. 5,151,092 issued to Buell et al. on Sep. 29, 1992. The elasticized waist feature and the elasticized side panel typically comprise an elastic member such as an elastomeric film affixed between portions of the absorbent article, for example, between the topsheet and the backsheet. The elasticized waist feature and elasticized side panels are thus, designed to expand and contract with the wearer's motions to maintain the fit of the absorbent article about the wearer during use.

However, it has been found that absorbent articles having elasticized waist features and elasticized side panels comprising elastomeric films can make the absorbent article feel hot and uncomfortable to wear because the elastomeric film is impermeable to air and/or moisture thereby making the diaper feel hot and uncomfortable in the waist region and in the side panels.

Therefore, it is an object of the present invention to provide a method for aperturing the portions of the diaper containing an elastomeric film, such as the waist feature portion and the side panel portion of the absorbent article.

It is a further object of the present invention to provide a method for aperturing a laminate at least one layer of which comprises thermoplastic material and the other layer comprises an elastic member.

These and other objectives of the present invention will be more readily apparent when considered in reference to the following description and when taken in conjunction with the accompanying drawings.

SUMMARY OF THE INVENTION

The present invention provides a method for aperturing a laminate. The first step is to provide a laminate comprising at least one nonwoven web comprised of thermoplastic fibers and at least one elastic member, such as an elastomeric film. The laminate is forwarded through a pressure biased nip comprising a relief patterned nip defining member having a plurality of pattern elements and a nip defining anvil member. The nip defining members are biased towards each other with a predetermined pattern-element loading. Each nip defining member is heated to a temperature that is sufficiently above the melt temperature of the thermoplastic fibers of the nonwoven web and above the melt temperature of the elastomeric film to enable aperturing of the laminate.

BRIEF DESCRIPTION OF THE DRAWINGS

While the specification concludes with claims particularly pointing out and distinctly claiming the subject matter which is regarded as forming the present invention, it is believed that the invention will be better understood from the following description which is taken in conjunction with the accompanying drawings and which like designations are used to designate substantially identical elements, and in which:

DETAILED DESCRIPTION OF THE INVENTION

As used herein, the term "absorbent article" refers to devices which absorb and contain body exudates, and more specifically, refers to devices which are placed against the skin of a wearer to absorb and contain the various exudates discharged from the body. The term "disposable" is used herein to describe absorbent articles which are not intended to be laundered or otherwise restored or reused as an absorbent article after a single use (i.e., they are intended to be discarded, and preferably, recycled, composted or otherwise disposed of in an environmentally compatible manner). A "unitary absorbent article" refers to an absorbent article which is formed from separate parts united together to form a coordinated entity so that they do not require separate manipulative parts like a separate holder and liner. A preferred embodiment of a unitary absorbent article comprising an elasticized waist feature and elasticized side panels apertured by the method of the present invention is the disposable absorbent article, disposable diaper 20, shown in FIG. 1. As used herein, the term "diaper" refers to an absorbent article generally worn by infants and incontinent persons that is generally worn about the lower torso of the wearer. It should be understood, however, that the present invention is also applicable to other absorbent articles such as incontinence briefs, diaper holders, feminine hygiene garments, training pants, and the like.

Figure 1:
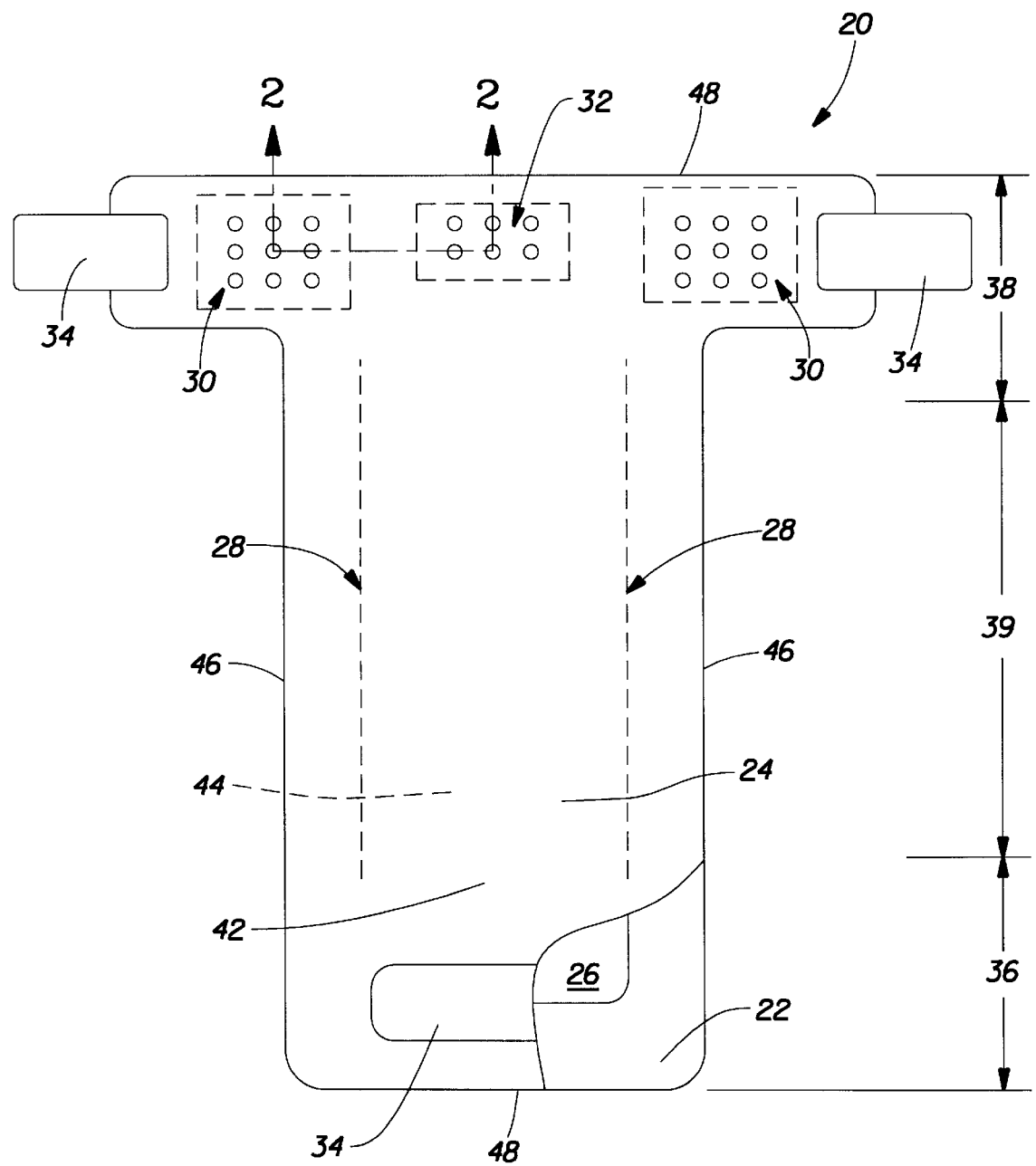
FIG. 1 is a plan view of an absorbent article comprising an apertured elasticized waist feature and apertured elasticized side panels both apertured in accordance with the method of the present invention.

With reference to FIG. 1, an absorbent article, such as diaper 20, generally comprises a topsheet 22, a backsheet 24 joined to the topsheet 22, and an absorbent core 26 positioned between the topsheet 22 and the backsheet 24. The diaper 20 preferably further comprises elasticized leg cuffs 28, elasticized side panels 30, an elasticized waist feature 32 and a fastening system 34.

The diaper 20 is shown in FIG. 1 to have an outer surface 42 (facing the viewer in FIG. 1), an inner surface 44 opposed to the outer surface 42, a front waist region 36, a rear waist region 38 opposed to the front waist region 36, a crotch region 39 positioned between the front waist region 36 and the rear waist region 38, and a periphery which is defined by the outer perimeter or edges of the diaper in which the longitudinal edges are designated 46 and the end edges are designated 48. The inner surface 44 of the diaper 20 comprises that portion of the diaper 20 which is positioned adjacent to the wearer's body during use (i.e., the inner surface 44 generally is formed by at least a portion of the topsheet 22 and other components joined to the topsheet 22). The outer surface 42 comprises that portion of the diaper 20 which is positioned away from the wearer's body (i.e., the outer surface 42 is generally formed by at least a portion of the backsheet 24 and other components joined to the backsheet 24). As used herein, the term "joined" encompasses configurations whereby an element is directly secured to the other element by affixing the element directly to the other element, and configurations whereby the element is indirectly secured to the other element by affixing the element to intermediate member(s) which in turn are affixed to the other element. The front waist region 36 and the rear waist region 38 extend from the end edges 48 of the periphery to the crotch region 39.

FIG. 1 shows a preferred embodiment of the diaper 20 in which the topsheet 22 and the backsheet 24 have length and width dimensions generally larger than those of the absorbent core 26. The topsheet 22 and the backsheet 24 extend beyond the edges of the absorbent core 26 to thereby form the periphery of the diaper 20.

The absorbent core 26 may be any absorbent means which is generally compressible, conformable, non-irritating to the wearer's skin, and capable of absorbing and retaining liquids such as urine and other body exudates. As shown in FIG. 1, the absorbent core 26 has a garment surface, a body surface, side edges, and waist edges. The absorbent core may be manufactured in a wide variety of sizes and shapes and from a wide variety of liquid-absorbent materials commonly used in disposable diapers and other absorbent articles such as commuted wood pulp, which is generally referred to as airfelt. Examples of other suitable absorbent materials include creped cellulose wadding; meltblown polymers including coform; chemically stiffened, modified or crosslinked cellulosic fibers; tissue including tissue wraps and tissue laminates; absorbent foams; absorbent sponges; superabsorbent polymer; absorbent gelling materials; or any equivalent material or combinations of materials. The configuration and construction of the absorbent core may also be varied (e.g., the absorbent core may have varying caliper zones, a hydrophilic gradient, a superabsorbent gradient, or lower average density and lower average basis weight acquisition zones; or may comprise one or more layers or substrates). The total absorbent capacity of the absorbent core, should, however, be compatible with the design loading and the intended use of the diaper 20. Further, the size and absorbent capacity of the absorbent core 26 may be varied to accommodate wearers ranging from infants through adults.

The backsheet 24 is preferably impervious to liquids (e.g., urine) and is preferably manufactured from a flexible material. As used herein, the term "flexible" refers to materials which are compliant and will readily conform to the general shape and contours of the human body. The backsheet prevents the exudates absorbed and contained in the absorbent core from wetting articles which contact the diaper 20 such as bed sheets and undergarments. The backsheet may thus comprise a woven or nonwoven material, polymeric films such as thermoplastic films of polyethylene or polypropylene, or composite material such as a film-coated nonwoven material. Preferably, the backsheet 24 is a thermoplastic film having a thickness of from about 0.012 mm (0.5 mil) to about 0.051 mm (2.0 mil).

The topsheet 22 is compliant, soft feeling, and non-irritating to the wearer's skin. Further, the topsheet is liquid pervious permitting liquids (e.g., urine) to readily penetrate through its thickness. A suitable topsheet may be manufactured from a wide range of materials, such as porous foams; reticulated foams; apertured plastic films; or woven or nonwoven webs of natural fibers (e.g., wood or cotton fibers), synthetic fibers (e.g. polyester or polypropylene fibers), or a combination of natural or synthetic fibers. Preferably, the topsheet is made of a hydrophobic material to isolate the wearer's skin from the liquids contained in the absorbent core. There are a number of manufacturing techniques which may be used to manufacture the topsheet 22. For example, the topsheet 22 may be a nonwoven web of thermoplastic fibers spunbonded, carded, wet-laid, meltblown, hydroentangled, combination of the above or the like. A preferred topsheet comprises a carded nonwoven web of thermoplastic fibers.

Figure 2:
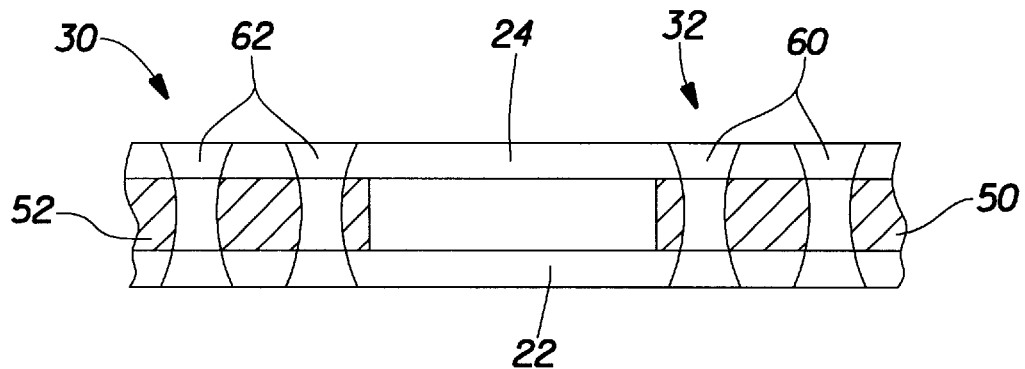
FIG. 2 is a fragmentary cross-sectional view of the diaper of FIG. 1 taken along section line 2—2.

FIG. 2 is a fragmentary cross-sectional view of the diaper 20 taken along section line 2—2 of FIG. 1 in the rear waist region 38. FIG. 2 shows the construction of the elasticized waist feature 32 and the elasticized side panel 30. The elasticized waist feature 32 preferably comprises a portion of the topsheet 22, a portion of the backsheet 24 and an elastic member 50 positioned between the topsheet 22 and the backsheet 24. The elasticized side panel 30 preferably comprises a portion of the topsheet 22, a portion of the backsheet 24 and an elastic member 52 positioned between the topsheet 22 and the backsheet 24.

In a preferred embodiment the elastic members 50 and 52 are bonded to both the topsheet 22 and the backsheet 24 using an adhesive. A glue applicator may be used to apply adhesive to the backsheet and/or the topsheet in those predetermined areas where the elastic members 50 and 52 will be placed. In a particularly preferred embodiment, the adhesive selected is stretchable and the glue applicator comprises a melt blown applicating system. Alternatively, the elastic members 50 and 52 may be bonded to the topsheet and/or the backsheet using other bonding methods known in the art.

The elastic members 50 and 52 may take on a number of different sizes, shapes, configurations and materials. Suitable elastic materials include "live" synthetic or natural rubber, synthetic or natural rubber foams, and elastomeric films including heat shrinkable elastomeric films.

The elasticized waist feature 32 contains apertures 60 which extend completely through the topsheet, the backsheet and the elastic member 50. The elasticized side panels 30 contain apertures 62 which also extend completely through the topsheet 22, the backsheet 24 and the elastic member 52. The apertures 60 and 62 permit the passage of air and vapor. As used herein, the term "aperture" refers to any opening that permits the passage of air and vapor. The apertures 60 and 62 may take on any size and shape. In addition, the apertures 60 and 62 may be arranged in patterns that are regular or irregular. In a preferred embodiment, the elasticized side panels 30 and the elasticized waist feature 32 comprise apertures having similar dimensions arranged in generally regular patterns. In preferred embodiments, the aperture density is between about 1 to about 1000 aperatures per square inch.

Figure 3:
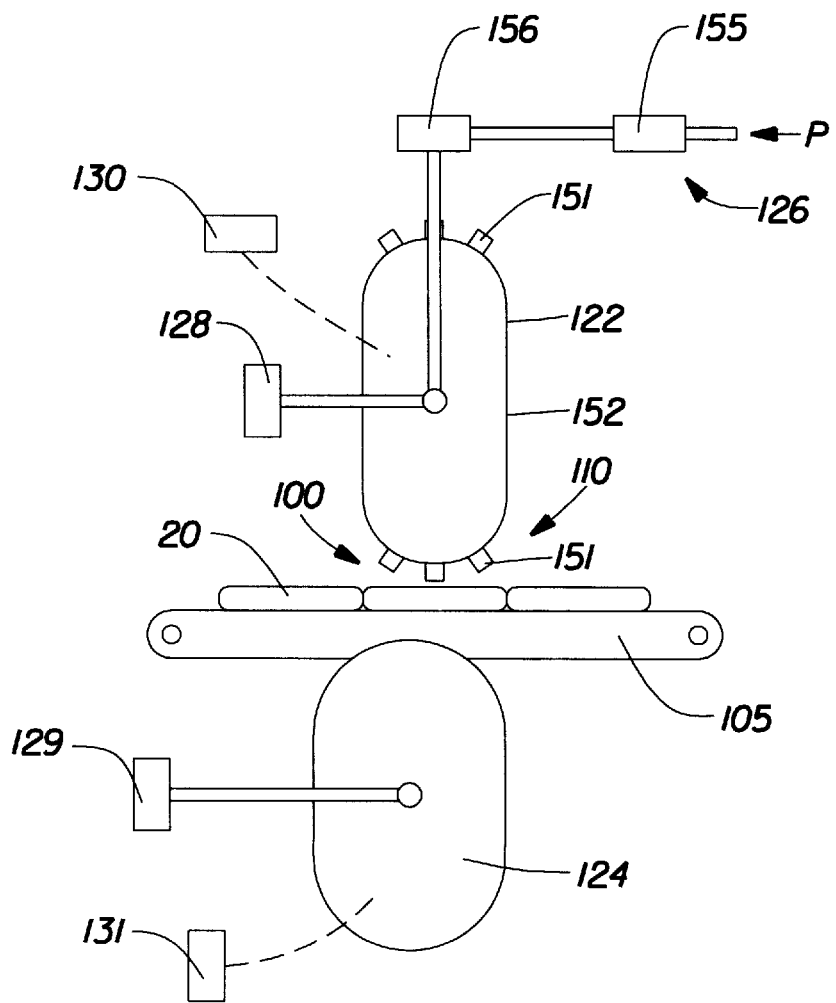
FIG. 3 is a fragmentary side elevational view of an exemplary apparatus embodiment of the present invention.

Referring now to FIG. 3, there is shown a method and apparatus for aperturing the elasticized waist feature 32 and the elasticized side panels 30 of the disposable diaper 20. A web 100 of innerconnected disposable diapers 20, such as the diaper 20 shown in FIG. 1 comprising an elasticized waist feature 32 and elasticized side panels 30 are fed on conveyor 105 to a dynamic and mechanical aperturing apparatus 110. Apparatus 110 comprises: pattern cylinder 122; anvil cylinder 124; means 126 for adjustably biasing cylinders 122 and 124 towards each other with a predetermined pressure within a predetermined range of pressures; means 128 and 129 for rotating cylinders 122 and 124, respectively, in independently controlled velocities; and temperature control means 130 and 131 for independently heating cylinders 122 and 124, respectively, to provide predetermined surface temperatures thereon.

For simplicity and clarity, apparatus 110 is described herein as comprising cylinders 122 and 124. However, cylinders are but exemplary nip defining members. Accordingly, it is not intended to thereby limit the invention to an apparatus comprising cylinders per se.

Briefly, referring to apparatus 110, the present invention enables the aperturing of a laminate, which laminate preferably comprises at least one nonwoven web comprised of thermoplastic fibers and at least one elastomeric film, by forwarding the laminate through a pressure biased nip comprising a patterned cylinder and an anvil cylinder. The patterned cylinder and the anvil cylinder are biased towards each other with a predetermined pattern-element loading and each is heated to a temperature that is sufficiently above the melt temperature of the thermoplastic fibers of the nonwoven web and above the melt temperature of the elastomeric film to enable aperturing of the laminate.

Patterned cylinder 122 is configured to have an oval surface 152, and a plurality of protuberances or pattern elements 151 which extend outwardly from surface 152. The protuberances 151 are disposed in a predetermined pattern: each patterned element being configured and disposed to precipitate an aperture in the diaper 20, such as in the elasticized waist feature 132 and the elasticized side panels 30. In a preferred embodiment, cylinders 122 and 124 are constructed of steel. However, cylinders 122 and 124 may be constructed of other suitable materials.

Means 126 for biasing pattern cylinder 122 towards anvil cylinder 124 comprises pressure regulating means 155, and pneumatic actuator means 156. Pressure regulating means 155 is adapted to have its inlet connect to a supply source P of pressurized air, and to have its outlet connected to pneumatic actuator means 156 in order to adjust and control the pneumatic actuator means loading of cylinders 122 and 124 towards each other. Whereas only one pneumatic actuator means 156 is visible in FIG. 3, identical actuators are in fact connected to each end journal of cylinder 122.

Drive means 128 and drive means 129 are provided to independently drive cylinders 122 and 124, respectively. Thus, they constitute means for power rotating the cylinders so that there is a predetermined but adjustable relationship between their surface velocities. This can be synchronous, or asynchronous: equal surface velocity; or with a predetermined surface velocity differential with either cylinder being driven faster than the other.

Temperature control means 130 and 131 are provided to adjustably control the surface temperatures of cylinders 122 and 124, respectively. These means enable the independent heating of the cylinders 122 and 124 to establish surface temperatures thereon that are sufficiently above the melt temperature of each individual layer of the laminate to be apertured.

Referring again to FIGS. 1 and 2, the laminate to be apertured preferably comprises a topsheet 22 comprising a nonwoven web of thermoplastic fibers, an elastic member such as elastomeric films 50 and 52, and a backsheet 24 comprising a nonwoven web of thermoplastic fibers. In order to effectively aperture the laminate shown in FIGS. 1 and 2 each cylinder 122 and 124 is heated to establish surface temperatures thereon that are sufficiently above the melt temperatures of the thermoplastic fibers of the nonwoven webs comprising the topsheet 22 and backsheet 24 above the melt temperature of the elastomeric films 50 and 52.

In another embodiment, the laminate preferably comprises a topsheet comprising a nonwoven web of thermoplastic fibers, an elastomeric film, and a backsheet comprising a thermoplastic film. Again, in order to effectively aperture the laminate, each cylinder is heated to establish surface temperatures thereon that are sufficiently above the melt temperatures of the thermoplastic fibers of the nonwoven web comprising the topsheet, above the melt temperature of the thermoplastic film comprising the backsheet, and above the melt temperature of the elastomeric film.

Figure 4:
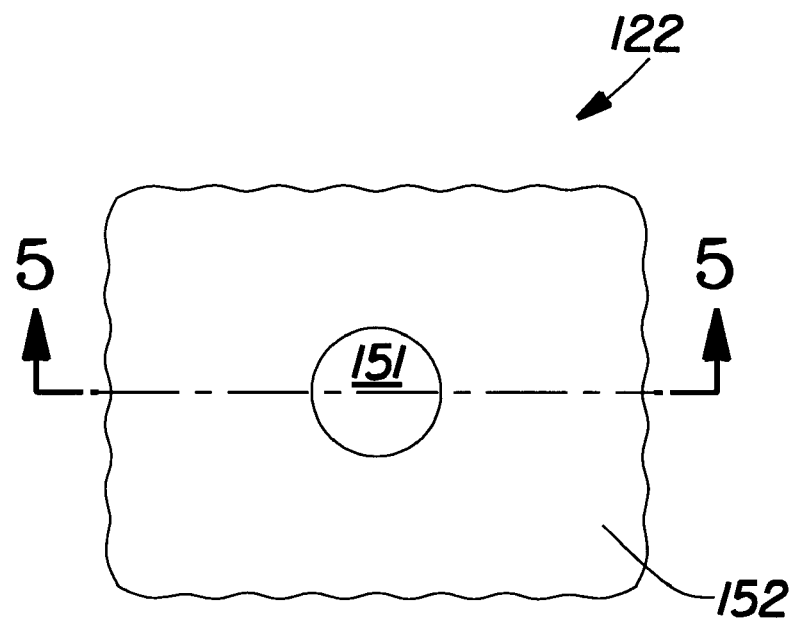
FIG. 4 is an enlarged fragmentary view looking radially inwardly toward a pattern element which is disposed on the surface of the patterned cylinder shown in FIG. 3.
Figure 5:
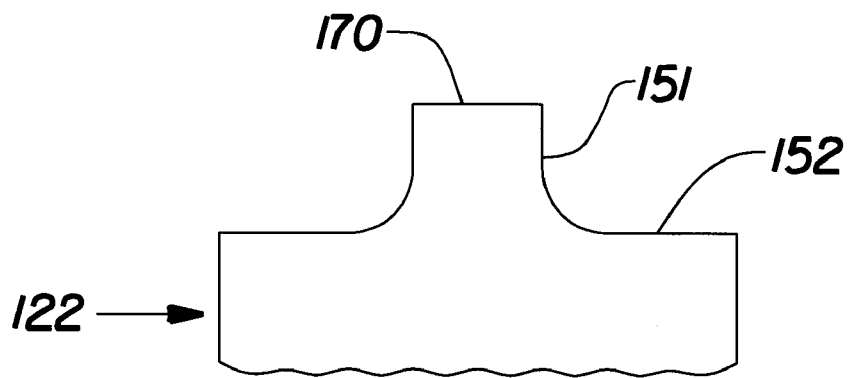
FIG. 5 is a fragmentary sectional view taken along section line 5—5 of FIG. 4.

Referring now to FIG. 4, a fragmentary portion of cylinder 122 is shown which comprises one pattern element 151 disposed on surface 152. FIG. 5 which is a fragmentary sectional view taken along section line 5—5 of FIG. 4, shows that the pattern element 151 is an integral portion of cylinder 122, has curvilinear side surfaces, and projects radially outwardly from the surface 152. In an exemplary embodiment, the outermost surface 170 of pattern element 151 has a circular plan form.

Figure 6:
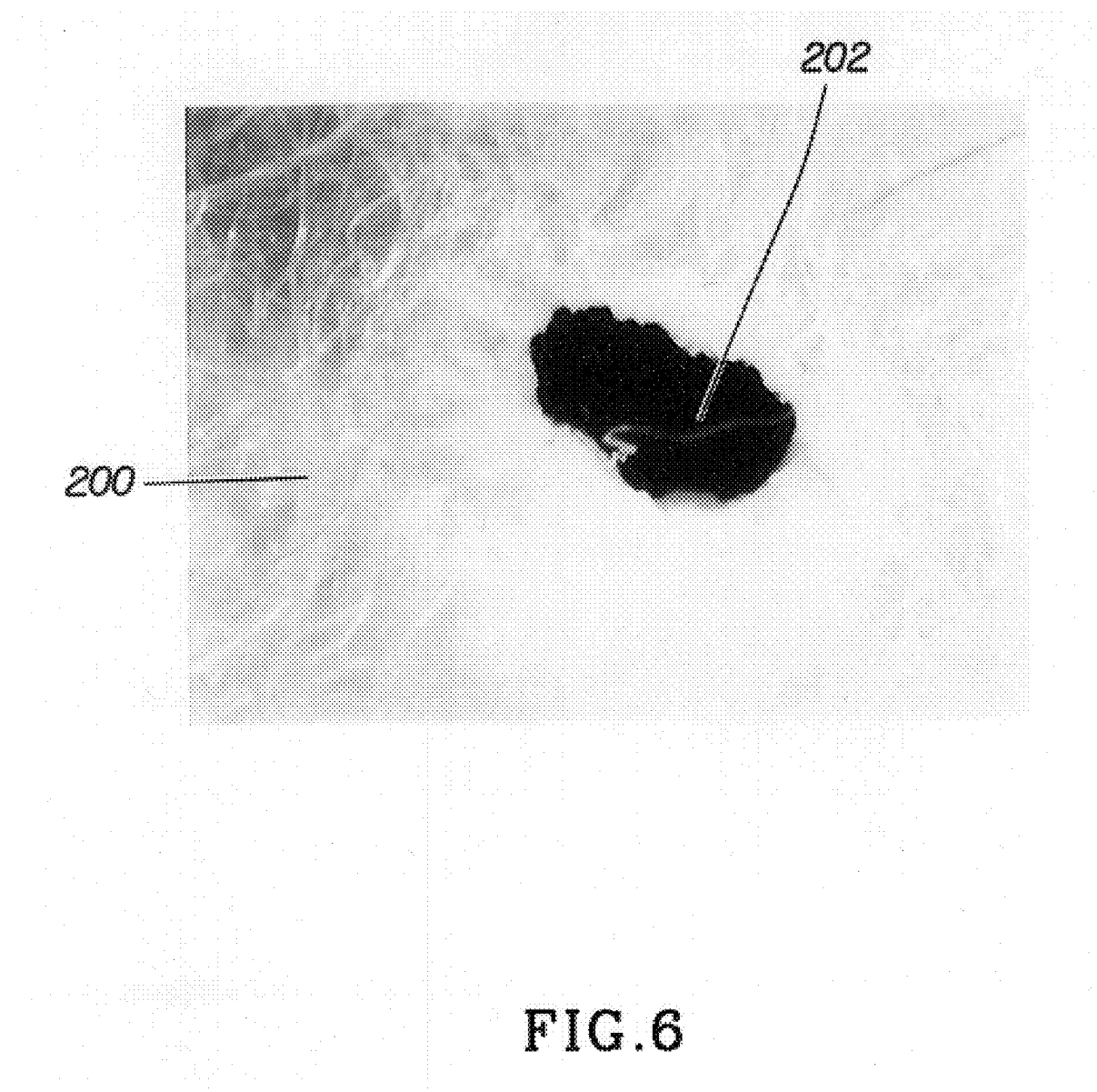
FIG. 6 is a photograph of a laminate which has been apertured according to the method of the present invention.

Referring now to FIG. 6, there is shown a photograph of a laminate 200 which has been apertured according to the method of the present invention. The laminate 200 comprises a nonwoven web, a polyethylene film, and an elastomeric film. As can be seen in FIG. 6, the laminate 200 has an aperture 202 therein. Aperture 202 has an annular ring about its periphery. The annular ring about the periphery of aperture 202 is formed by the melting of the laminate materials. Melting is due to the heat of the cylinders and friction from compression of the material. In addition, the annular ring is stretched by the pressure in the nip pushing it away from the center. As it cools and solidifies the ring gathers or puckers. Because of this, when the laminate is stretched in use, no stress is placed on the annular ring until the puckering is pulled out yielding a higher total stretch capability before the annular ring tears. This annular ring serves to preserve the integrity of the aperture 202 during stretching and/or wear of the absorbent article. Accordingly, when a laminate of the above composition forms the waist portion or side portions of a disposable absorbent article it is subjected to normal wearing forces and is extended via the elastomeric member contained therein. As the laminate is stretched and subjected to normal wearing forces, the annular ring prevents the initiation of tearing thus maintaining the integrity of the laminate.

The laminate 200 of FIG. 6 was apertured by heating the nip defining members to a temperature that is sufficiently above the melt temperature of the thermoplastic fibers of the nonwoven web, above the melt temperature of the polymeric film, and above the melt temperature of the elastic member. In this instance, the nip defining members were heated to a temperature in excess of 124° C.

It is important to note that excessive heating can negatively affect the stretch properties of the laminate. For example, as the temperature of the nip defining members increases, the amount of material which melts to form the annular ring also increases. The melted material forming the annular ring exhibits less stretch than the unmelted portions of the laminate material surrounding the annular ring. However, there is a trade off between tearing at the apertures and the stretch of the laminate material. As the temperature of the nip defining members is increased, the tearing of the laminate material is reduced. This phenomenon is believed to be caused by the fact that better reinforcement and gathering of material around the perimeter of the apertures is formed by the temperature increase of the nip defining members. Therefore, one must heat the nip defining members to a temperature such that the desired stretch properties of the laminate and the tear properties of the laminate are achieved as a balance between the two needs to be struck to provide the desired performance.

In addition, the size of the apertures is also determined by the temperature at which the nip defining members are heated. As would be expected, as the temperature of the nip defining members is increased, the size of the apertures created in the laminate also increases.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for aperturing a laminate, said laminate comprising at least one nonwoven web comprised of thermoplastic fibers, a thermoplastic film, and at least one elastic member, said method comprising the steps of:

a) forwarding said laminate through a pressure biased nip comprising a relief patterned nip defining member having a plurality of pattern elements and a nip defining anvil member;

b) biasing said nip defining members towards each other with a predetermined patterned-element pressure;

c) heating each nip defining member to a temperature that is sufficiently above the melt temperature of said thermoplastic fibers of said nonwoven web and above the melt temperature of said thermoplastic film and said elastic member to form an aperture in said laminate and to form an annular ring about the periphery of said aperture wherein said pressure between said nip members pushes said annular ring away from its center to stretch said annular ring; and d) cooling and solidifying said annular ring to gather or pucker said annular ring so as to preserve the integrity of said aperture during subsequent stretching of the said laminate thereby yielding a higher total stretch capability of the said laminate before said annular ring tears.

2. The method of claim 1 wherein said laminate is selected from the group consisting of an elasticized waist feature and an elasticized side panel.

3. The method of claimed 1 wherein said laminate comprises a pair of nonwoven webs comprised of thermoplastic fibers.

4. The method of claim 1 wherein said thermoplastic film comprises a polyethylene film.

5. The method of claim 1 wherein said predetermined pattern-element pressure is at least about 100,000 psi.

6. The method of claim 1 wherein said elastic member comprises an elastomeric film.

* * * * *